United States Patent [19]

Nalepa

[11] Patent Number: 4,727,191

[45] Date of Patent: Feb. 23, 1988

[54] PURIFICATION OF (HYDROCARBYLTHIO) AROMATIC AMINES

[75] Inventor: Christopher J. Nalepa, Baton Rouge, La.

[73] Assignee: Ethyl Corporation, Richmond, Va.

[21] Appl. No.: 884,202

[22] Filed: Jul. 10, 1986

[51] Int. Cl.⁴ .............................................. C07C 85/26
[52] U.S. Cl. .................................... 564/437; 564/430; 564/440; 546/293; 548/484; 548/541; 568/38; 568/57
[58] Field of Search ...................... 564/437, 440, 430; 546/293; 548/484, 541; 568/38, 57

[56] References Cited

U.S. PATENT DOCUMENTS

| | | | |
|---|---|---|---|
| 3,228,989 | 1/1966 | Reifschneider | 568/57 |
| 3,763,239 | 10/1973 | Smolin | 564/437 |
| 3,931,321 | 1/1976 | Planker et al. | 564/437 |
| 4,594,453 | 6/1986 | Ranken et al. | 564/440 |

*Primary Examiner*—Anton H. Sutto
*Assistant Examiner*—John A. Sopp
*Attorney, Agent, or Firm*—Donald L. Johnson; John F. Sieberth; Patricia J. Hogan

[57] ABSTRACT

A (hydrocarbylthio)aromatic amine, such as a methylthiosubstituted toluenediamine, is separated from corresponding aromatic amines containing fewer hydrocarbylthio groups by washing an organic solution of the amine mixture with a dilute aqueous acid having a pKa value below 7 to extract at least a portion of the corresponding aromatic amines.

8 Claims, No Drawings

PURIFICATION OF (HYDROCARBYLTHIO) AROMATIC AMINES

FIELD OF INVENTION

This invention relates to (hydrocarbylthio)aromatic amines and more particularly to a process for purifying them.

BACKGROUND

As disclosed in U.S. Pat. No. 4,594,453 (Ranken et al.), it is known that (hydrocarbylthio)aromatic amines can be prepared by reacting an aromatic amine with a hydrocarbyl disulfide in the presence of a catalytic amount of a Lewis acid. This process typically results in the formation of a mixture of hydrocarbylthiation products, and it is frequently desirable to resolve the mixture—at least to the extent of separating the products having different degrees of hydrocarbylthiation from one another and/or from any unreacted aromatic amine. When small research quantities are involved, this separation can be accomplished by distillation. However, distillation has been found to be unsatisfactory when larger quantities are involved because of the product degradation that occurs during prolonged heating at distillation temperatures.

U.S. Pat. No. 3,763,239 (Smolin) teaches that certain diamines can be extracted from monoamines with an aqueous mineral acid.

SUMMARY OF INVENTION

An object of this invention is to provide a novel process for purifying (hydrocarbylthio)aromatic amines.

Another object is to provide such a process wherein (hydrocarbylthio)aromatic amines are separated from aromatic amines having different degrees of hydrocarbylthiation.

These and other objects are attained by washing an organic solution of a (hydrocarbylthio)aromatic amine which is in admixture with at least one corresponding aromatic amine containing fewer hydrocarbylthio groups with a dilute aqueous acid having a pKa value below 7 to extract at least a portion of the corresponding aromatic amine.

DETAILED DESCRIPTION (Hydrocarbylthio)aromatic amines that can be purified in the practice of the invention are aromatic compounds bearing one or more hydrocarbylthio substituents on a carbocyclic or heterocyclic ring (e.g., a benzene, naphthalene, pyrrole, pyridine, indole, etc., ring) which has an amino nitrogen in the ring and/or bears one or more amino groups on the ring and which may bear additional substituents, such as chloro, fluoro, alkyl, alkoxy, aryl, aryloxy, alkaryl, or aralkyl substituents, e.g., all of the (hydrocarbylthio)aromatic amines that may be prepared by the process of Ranken et al., the teachings of which are incorporated herein in toto by reference.

Thus, the amines include, e.g., the mono- and polyhydrocarbylthio compounds prepared by reacting a hydrocarbyl disulfide (e.g., methyl, ethyl, propyl, n-butyl, sec-butyl, t-butyl, 2-chloropentyl, cyclopentyl, cyclohexyl, phenyl, benzyl, p-tolyl, or p-chlorophenyl disulfide) with an aromatic amine (e.g., 4,4'-methylenedianiline, 1,3-dimethylpyrrole, 1-methylpyrrole, 2-aminobiphenyl, 4-phenoxyaniline, 7-methylindole, aniline, 4-butylaniline, 4-methylaniline, 4-chloroaniline, 2-ethylaniline, N-methylaniline, 1,5-diaminonaphthalene, 2,6-diaminopyridine, 1,2-, 1,3-, and 1,4-diaminobenzenes, 2,4- and 2,6-diaminotoluenes, 2,4- and 2,6-diamino-1-ethylbenzenes, etc.) in the presence of a Lewis acid, such as a boron, aluminum, ferrous, ferric, cuprous, cupric, zinc, cadmium, lead, cobaltous, mercurous, or mercuric chloride, bromide, or iodide, a reactive metal (e.g., aluminum), a metal alkyl (e.g., triethylaluminum, diethylaluminum chloride, etc.), etc.

As mentioned above, these (hydrocarbylthio)aromatic amines, as prepared, are typically in admixture with at least one corresponding aromatic amine having a different degree of hydrocarbylthiation, i.e., an aromatic amine having the same structure as the (hydrocarbylthio)aromatic amine to be purified except for having no hydrocarbylthio groups or a different number of hydrocarbylthio groups on the aromatic ring. For example, a desired di(hydrocarbylthio)aromatic amine or mixture of di(hydrocarbylthio)aromatic amines is apt to be in admixture with an aromatic amine having no hydrocarbylthiation on the ring, with one or more mono(hydrocarbylthio)aromatic amines, and with one or more tri(hydrocarbylthio)aromatic amines. It is such mixtures that are treated in the practice of the present invention.

In a preferred embodiment of the invention, the (hydrocarbylthio)aromatic amine that is purified is a (hydrocarbylthio)aromatic diamine, especially such a diamine wherein the hydrocarbylthio groups are alkylthio groups containing 1-6 carbons, e.g., a (methylthio)-toluenediamine.

To facilitate contact with the acid, the crude (hydrocarbylthio)aromatic amine is dissolved in an organic solvent prior to the acid treatment. The solvent employed may be any suitable solvent, i.e., any organic solvent which is not appreciably soluble in water. Such solvents include, e.g., hydrocarbons, chlorinated hydrocarbons, esters, and ethers, such as toluene, hexane, heptane, methylene chloride, chloroform, ethyl acetate, diethylether, etc.

The acid used to treat the crude amine may be any acid strong enough to have a pKa value below 7, although nitric acid and other strong oxidizing acids are generally avoided because of their giving violent reactions. Exemplary of utilizable acids are inorganic acids such as hydrochloric, sulfuric, phosphorous, and phosphoric acids, sodium hydrogen sulfate, etc., and organic acids such as acetic, chloroacetic, methanesulfonic, benzoic, etc., with sulfuric and phosphoric acids being especially preferred.

As mentioned above, the acid is employed in the form of a dilute aqueous solution, generally a 0.5-50% solution—the amount used varying with the amount of contaminating amine to be extracted. In any particular instance, the amount of acid should be at least one mol per mol of amine to be extracted and is generally at least slightly in excess of the required amount.

In the process of the invention, the crude amine solution is washed with the aqueous acid to provide an intimate contact that results in gradually extracting the amines into the aqueous phase in increasing order of degree of hydrocarbylthio substitution—the amines having no hydrocarbylthio substitution being extracted first, then the amines bearing one hydrocarbylthio substituent, then the amines bearing two hydrocarbylthio substituents, etc. Thus, by controlling the amount of aqueous acid used, it is possible to extract each of the homologs sequentially in separate washes to provide each of the amines in purer form, to extract all of the homologs having a lower-than-desired degree of hydrocarbylthiation with a larger wash to provide an aqueous amine mixture that may then be discarded or treated to isolate each of its components, etc.

When an amine or amine mixture has been extracted by the aqueous acid, it may be removed from the unextracted amine or amines having higher degrees of hydrocarbylthiation by allowing the organic and aqueous phases to separate. The aqueous phase may then be discarded or, when its amine content is desired, treated by conventional means (e.g., neutralization with a base, followed by extraction with an organic solvent) to recover the extracted amine or amines. In instances where the amount of aqueous acid employed in the first extraction was such as to extract aromatic amines having more than one degree of hydrocarbylthiation, the amines recovered from the aqueous phase can then be subjected to one or more additional acid extractions to effect more complete separation.

When a desired amine has an intermediate degree of hydrocarbylthiation, it is generally purified by conducting one or more acid washes and phase separations to remove the amines having lower degrees of hydrocarbylthiation, then washing the remaining amine mixture with an amount of aqueous acid such as to extract the desired amine without extracting amines having a higher degree of hydrocarbylthiation, and finally—after phase separation—recovering the desired amine from the aqueous phase.

The invention is advantageous as an economical, efficient method of recovering (hydrocarbylthio)aromatic amines under conditions mild enought to avoid product degradation.

The following examples are given to illustrate the invention and are not intended as a limitation thereof.

EXAMPLE I

Part A

A crude methylthiated 2,4-toluenediamine was prepared by reacting 5.77 mols of dimethyldisulfide with 2.79 mols of 2,4-toluenediamine in the presence of 0.203 mol of aluminum chloride over a period of 27 hours, removing excess dimethyldisulfide, diluting the reaction mixture with 850 mL of toluene, and treating it with 500 mL of 1.5M sodium hydroxide to form a reaction mixture having the following analysis:

| Component | VPC Area % |
|---|---|
| 2,4-toluenediamine | 1.4 |
| mono(methylthio)-2,4-toluenediamines | 34.2 |
| 3,5-di(methylthio)-2,4-toluenediamine | 63.5 |
| di- and tri(methylthio)-1,3-diaminobenzenes | 0.8 |

Part B

The crude reaction mixture of Part A was washed with 10% aqueous phosphoric acid (3×650 mL), after which analysis of the toluene layer showed:

| Component | VPC Area % |
|---|---|
| mono(methylthio)-2,4-toluenediamines | 0.9 |
| 3,5-di(methylthio)-2,4-toluenediamine | 98.2 |
| di- and tri(methylthio)-1,3-diaminobenzenes | 0.8 |

This purer 3,5-di(methylthio)-2,4-toluenediamine was recovered by removing the toluene.

Part C

The combined acid washed from Part B were neutralized with 200 g of sodium hydroxide, followed by toluene extraction (300 mL, 150 mL). The toluene layers were then washed with 1% aqueous phosphoric acid (900 mL, 300 mL) to remove 2,4-toluenediamine, and the toluene was evaporated to leave a dark orange oil having the following analysis:

| Component | VPC Area % |
|---|---|
| mono(methylthio)-2,4-toluenediamines | 92.3 |
| 3,5-di(methylthio)-2,4-toluenediamine | 6.7 |

EXAMPLE II

Following the same general procedure as in Example I, a commercial mixture of 80% 2,4-toluenediamine and 20%, 2,6-toluenediamine was methylthiated to form a crude reaction mixture which was then diluted with toluene and washed with 10% phosphoric acid to remove contaminants. The reaction mixture, prior to the phosphoric acid wash, had the following analysis:

| Component | VPC Area % |
|---|---|
| toluenediamines | 1.1 |
| mono(methylthio)toluenediamines | 26.4 |
| di(methylthio)toluenediamines | 69.8 |
| di- and tri(methylthio)-1,3-phenylenediamines | 1.5 |

After the phosphoric acid wash, the toluene layer had the following analysis.

| Component | VPC Area % |
|---|---|
| mono(methylthio)toluenediamines | 0.3 |
| di(methylthio)toluenediamines | 96.0 |
| di- and tri(methylthio)-1,3-phenylenediamines | 2.3 |

EXAMPLE III

Part A

A crude product was prepared by reacting 2.79 mols of the commercial toluene mixture of Example II with 6.56 mols of diethyldisulfide in the presence of 0.12 mol of zinc iodide for 43 hours and then removing excess disulfide. The reaction mixture was diluted with 750 mL of toluene, and analysis showed the following composition:

| Component | VPC Area % |
| --- | --- |
| toluenediamines | 15.1 |
| mono(ethylthio)toluenediamines | 52.6 |
| di(ethylthio)toluenediamines | 31.7 |
| di- and tri(ethylthio)-1,3-diaminobenzenes | trace |

Part B

The crude reaction mixture of Part A was washed with 10% aqueous phosphoric acid (4×650 mL, 200 mL), after which analysis of the toluene layer showed:

| Component | VPC Area % |
| --- | --- |
| mono(ethylthio)toluenediamines | 1.0 |
| di(ethylthio)toluenediamines | 97.5 |
| di- and tri(ethylthio)-1,3-diaminobenzenes | 0.8 |

EXAMPLE IV

A reaction mixture prepared by the ethylthiation of three mols of 1,3-diaminobenzene and having the following analysis:

| Component | VPC Area % |
| --- | --- |
| di(ethylthio)-1,3-diaminobenzenes | 23.0 |
| 2,4,6-tri(ethylthio)-1,3-diaminobenzenes | 77.0 | was diluted with 2 L of toluene and washed with 25% sulfuric acid (2×2 L). The organic layer was then treated with 50% sodium hydroxide (0.5 L) and water (2×0.5 L), and the toluene was removed to provide an oil having the following analysis:

| Component | VPC Area % |
| --- | --- |
| di(ethylthio)-1,3-diaminobenzenes | 2.2 |
| 2,4,6-tri(ethylthio)-1,3-diaminobenzenes | 97.8 |

It is obvious that many variations may be made in the products and processes set forth above without departing from the spirit and scope of this invention.

What is claimed is:

1. A process which comprises washing an organic solution of a (hydrocarbylthio)aromatic amine which is an admixture with at least one corresponding aromatic amine containing fewer hydrocarbylthio groups with a dilute aqueous acid having a pKa value below 7 to extract at least a portion of the corresponding aromatic amine.

2. The process of claim 1 wherein the (hydrocarbylthio)aromatic amine is an aromatic diamine wherein the hydrocarbylthio groups are alkylthio groups containing 1-6 carbons.

3. The process of claim 2 wherein the (hydrocarbylthio)aromatic amine is 3,5-di(methylthio)-2,4-toluenediamine.

4. The process of claim 2 wherein the (hydrocarbylthio)aromatic amine is a mixture of 3,5-di(methylthio)-2,4-toluenediamine and 3,5-di(methylthio)-2,6-toluenediamine.

5. The process of claim 2 wherein the (hydrocarbylthio)aromatic amine is a di- or tri(methylthio)-1,3-diaminobenzene.

6. The process of claim 1 wherein the acid is phosphoric acid.

7. The process of claim 1 wherein the acid is sulfuric acid.

8. The process of claim 1 wherein the amount of acid is at least one mol per mol of corresponding aromatic amine to be extracted.

* * * * *